(12) United States Patent
Liu

(10) Patent No.: US 7,857,619 B2
(45) Date of Patent: Dec. 28, 2010

(54) LED CURING LIGHT HAVING FRESNEL LENSES

(76) Inventor: Yongqian Liu, 4404 Breckinridge Blvd., Richardson, TX (US) 75082

( * ) Notice: Subject to any disclaimer, the term of this patent is extended or adjusted under 35 U.S.C. 154(b) by 0 days.

(21) Appl. No.: 11/307,813

(22) Filed: Feb. 24, 2006

(65) Prior Publication Data

US 2007/0275344 A1    Nov. 29, 2007

Related U.S. Application Data

(60) Provisional application No. 60/593,954, filed on Feb. 26, 2005.

(51) Int. Cl.
*A61C 1/00* (2006.01)
*G02B 27/10* (2006.01)
*G02B 3/08* (2006.01)

(52) U.S. Cl. .......................... 433/29; 359/622; 359/742
(58) Field of Classification Search ............... 433/29, 433/140, 215; 362/119; 359/622, 742
See application file for complete search history.

(56) References Cited

U.S. PATENT DOCUMENTS

| | | | |
|---|---|---|---|
| 5,128,848 A * | 7/1992 | Enders et al. | 362/268 |
| 5,634,711 A * | 6/1997 | Kennedy et al. | 362/119 |
| 5,813,743 A * | 9/1998 | Naka | 362/16 |
| 5,940,152 A * | 8/1999 | Wilson et al. | 349/57 |
| 5,995,071 A * | 11/1999 | Mertz | 345/84 |
| 6,419,483 B1 | 7/2002 | Adam | 433/29 |
| 6,611,110 B1 | 8/2003 | Fregoso | 315/224 |
| 6,692,250 B1 * | 2/2004 | Decaudin et al. | 433/29 |
| 6,692,251 B1 * | 2/2004 | Logan et al. | 433/29 |
| 6,702,576 B2 | 3/2004 | Fischer | 433/29 |
| 6,755,647 B2 | 6/2004 | Melikechi | 433/29 |
| 2002/0191297 A1 * | 12/2002 | Gleckman et al. | 359/629 |
| 2003/0090813 A1 * | 5/2003 | Servatius et al. | 359/742 |
| 2003/0133203 A1 | 7/2003 | McLean | 359/708 |
| 2004/0090794 A1 * | 5/2004 | Ollett et al. | 362/555 |
| 2004/0114229 A1 * | 6/2004 | Sakaguchi | 359/460 |
| 2004/0228142 A1 * | 11/2004 | Takada et al. | 362/555 |
| 2004/0239243 A1 * | 12/2004 | Roberts et al. | 313/512 |
| 2004/0258563 A1 * | 12/2004 | Young et al. | 422/58 |
| 2005/0196721 A1 | 9/2005 | Jackson, III | 433/29 |
| 2006/0018123 A1 | 1/2006 | Rose | 362/341 |

* cited by examiner

*Primary Examiner*—Cris L Rodriguez
*Assistant Examiner*—Heidi M Eide
(74) *Attorney, Agent, or Firm*—Jackson Walker L.L.P.; Christopher J. Rourk

(57) ABSTRACT

Disclosed is a LED curing light device for curing of photo-polymerization materials. The device has a plurality of LED sources and a plurality of Fresnel lenses. The LED source is powered and controlled by a drive board and batteries providing high power curing light in the range of 300 to 500 nm and optical power in the range of 100 to 800 mW. The Fresnel lenses couple the curing light efficiently to a focused spot on a curing object

20 Claims, 5 Drawing Sheets

LED CURING LIGHT HAVING FRESNEL LENSES

CROSS-REFERENCE TO RELATED APPLICATIONS

This application claims priority to provisional patent application Ser. No. 60/593,954, filed Feb. 26, 2005 and patent application Ser. No. 10/906,772, filed Mar. 5, 2005.

FIELD OF THE INVENTION

The invention relates generally to the field of light curing device, and more particularly to medical curing device and methods for irradiating and curing photosensitive curing compounds.

BACKGROUND OF THE INVENTION

Photosensitive compounds or adhesives are commonly used in bonding object surfaces together or for filling openings and cavities in an object surface. They are cured by exposure to radiation energy, such as UV with a wavelength between 300 to 400 nm or blue light with a wavelength between 400 to 500 nm. Medical curing light device are commonly used in dentistry, endoscopies, and plastic surgeries. In the field of dentistry, curable adhesives and dental curing apparatus are common practice in restoration and cosmetic procedures using restorative materials, dental sealants and orthodontic adhesives to bond brackets to the surfaces of teeth. Curing light is also widely used in device, component and circuit board packaging using photo-initiator activated composites to bond two different surfaces or protect components.

Traditionally, curing light apparatus are implemented with bulk lamps such as tungsten-halogen lamps coupled into fiber optic waveguide that delivers light to expose area of adhesives need to be cured. Recent advances in light emitting diodes (LEDs) technologies have enabled a new class of curing light apparatus with smaller size, longer lifetime and lower cost by semiconductor light emitting chips.

LEDs emit light at selected wavelengths of absorption band of photo-initiators that start the curing process of curable adhesives. Typical wavelength for dental curing is in the range of 400-500 nm. It is highly desirable to have high optical density impinged on the curable adhesives to activate the photo-initiators that allow a quick curing time of between 2 to 10 seconds and a deeper curing depth of between 2 to 6 millimeters. Typical ranges of optical density for a desirable 4 to 5 millimeters curing depth and less than 10 seconds curing time are above 1000 mW/cm$^2$. In dental applications, such intensity is exposed to the curing area, typically in the range of 2 to 6 mm dimension, limited by the cavity and bracket size.

There have been two approaches in the selection of LEDs to achieve such high intensity, namely single high power LEDs or multiple standard single diode LEDs. High power LEDs integrates multiple LED chips in a single package such as LEDs made by Lumiled's Luxeon product lines that generate optical power as high as 800 mW. Standard single chip LEDs generates optical power below 150 mW. Typical arrangements of more than five LEDs are required to deliver equivalent power at the curing site. Other critical elements of efficient curing are the light delivering system and working distance of the curing apparatus from the curing object for efficient cure.

U.S. Pat. No. 6,611,110 describes an apparatus using light guides to deliver curing light from a single LED to the curing site. The light guide reduces the deliverable curing light efficiency due to optic coupling, transmission, and diffraction losses from light guide with a typical total efficiency of below 30%. A higher power LED can compensate the loss. Additional use of lens such as total internal reflection (TIR) lens as described in U.S. Pat. No. 6,692,251 can improve the power density. However, they introduce higher cost and more cumbersome system. Additionally, it has been shown that autoclaving the light guide to sterilize the apparatus can reduce the transmission performance of the light guide making them costly to replace.

U.S. Pat No. 20030133203 describes an apparatus using a bulk aspheric lens to directly focus curing light from a single LED to the curing site. The aspheric lens is molded glass or plastic lens. The benefit of such implementation is a reduced size and cost compared to using of light guide. However, a high power LED is highly non-directional typically following a Lambertian radiation pattern with radiation angles above 120 degrees at half of its maximum intensity. Combined with a source chip size of typically 3 millimeter, the LED radiation incurs collection loss through the aspheric lens and diffracts quickly to lose its intensity due to limited collection angles that aspheric lens offer, which is typically less than 70 degrees. Aspheric lenses with short focal length to collect light from LED source are also thick with aspect ratio of diameter to thickness close to one enlarging the size of the apparatus as well. Working distances of such devices are typically limited to a short distance within a few millimeters. In addition, sterilizing tubes to protect the lens entrance will significantly reduce radiation due to optical diffractions.

A need exists, therefore, for improved LED curing apparatus that provide efficient light delivery to the curing site at high optical intensity with low cost particularly in the dental applications.

SUMMARY OF THE INVENTION

Accordingly, it is a principal object of the present invention to overcome the disadvantages of prior art methods of dental curing light system. The present invention comprises a method, and resulting apparatus, for highly efficient curing system for curable materials, in particular for dental curing.

In one embodiment, the optical device of the invention includes a high power LED source and a single Fresnel lens placed at a distance larger than its focal length to the LED source to collect radiation up to 160 degrees and focus the radiation into a curing spot.

In another embodiment, the optical device of the invention includes a high power LED source. The LED illumination is captured by a Fresnel lens with collection angles approximately between 100 to 160 degrees into diffraction limited collimating beam and then focused into a spot diameter approximately less than 5 millimeters by a second Fresnel lens placed in close proximity to the first lens. The pair of Fresnel lenses is bonded together into an efficient lens with two flat surfaces on the outside and lens grooves bonded in-between with a total thickness approximately between 0.5 to 2 millimeters. The exit window of the lens pair is shielded and protected by a sterilizable and disposable cone-shaped plastic cap.

In one embodiment of implementing the invention, the optical device of the invention includes a high power LED source placed within a parabolic reflector that works also as a lens mount for a plurality of Fresnel lenses to focus the emitted light from the LED to a small spot size of approximately under 4 mm at the curing composite.

In one embodiment of implementing the invention, the optical device is integrated with a handpiece containing control electronics and rechargeable batteries that activate the high power LED being focused to a small spot of approximately under 4 mm by the Fresenl lenses at the curing composite.

It is to be understood that both the foregoing general descriptions and the following detailed description are merely exemplary of the invention, and are intended to provide an overview or framework for understanding the nature and character of the invention as it is claimed. Additional features and advantages of the invention will become apparent from the following drawings and description. The drawings illustrate various embodiments of the invention and together with the description serve to explain the principles and operations of the invention.

BRIEF DESCRIPTION OF THE DRAWINGS

The above and further advantages of this invention may be better understood by referring to the following description taken in conjunction with the accompanying drawings in which like numerals designate corresponding elements or sections throughout, and in which.

DETAILED DESCRIPTION OF THE PREFERRED EMBODIMENTS

Figure 1:
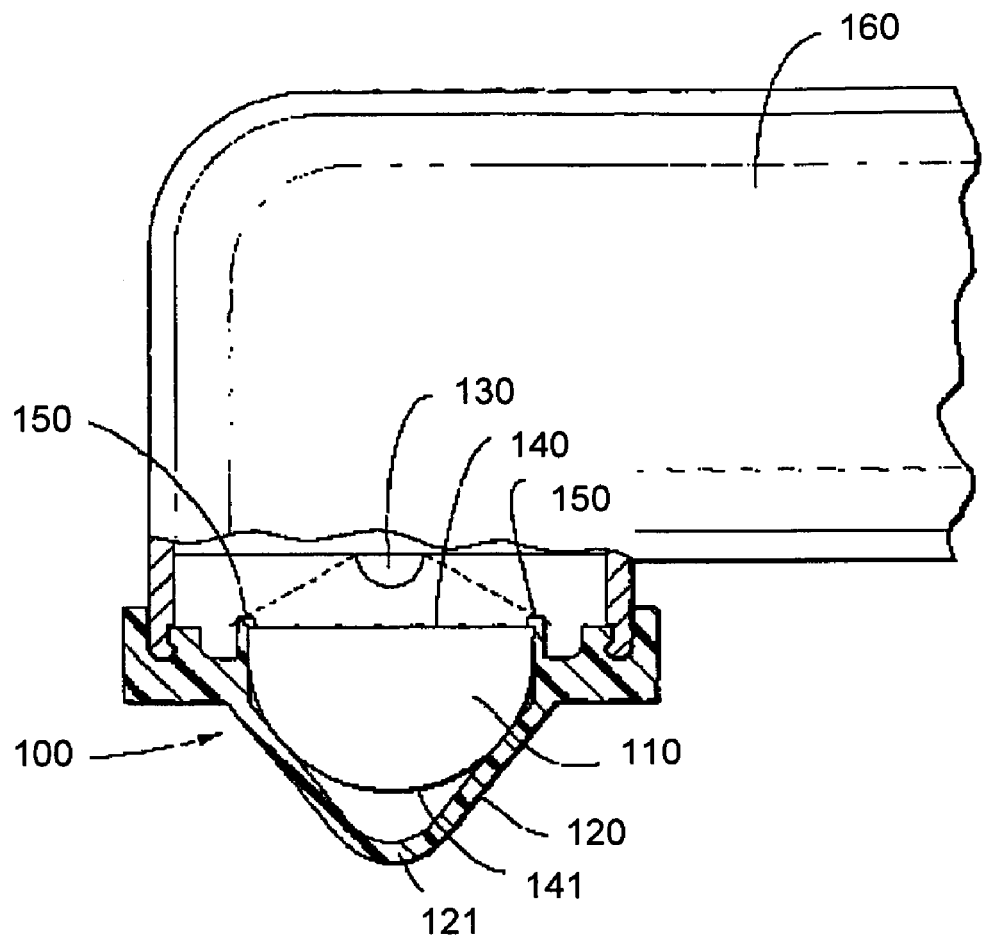
FIG. 1 shows a prior dental LED curing method using bulk aspheric lens.

FIG. 1 shows a prior art dental LED curing light device 100 consisting of a LED 130, an aspheric lens 110, and a transparent shield 120 all attached to an extension arm 160. The aspheric lens 110 comprises of a first end 140, which is substantially flat, and a second end 141 that has an aspheric curvature. The transparent shield has an apex 121 to ease use for insertion into a dental cavity and clips 150 to wrap around and secure the lens 110 in place. The aspheric lens is preferably composed of a transparent material such as glass, aluminum dioxide, sapphire, quartz, acrylic, polyacrylic, polypropylene, and silicone. Apparatus using standard aspheric lenses as described are limited by the performances of the optical parameters of such lens with collection angle typically less than 70 degrees and thickness of approximately between 0.1 to 5 millimeters or more than 3 millimeters due to high curvature required to have short focal length. As a result, they are not efficient in focusing curing light.

Figure 2:
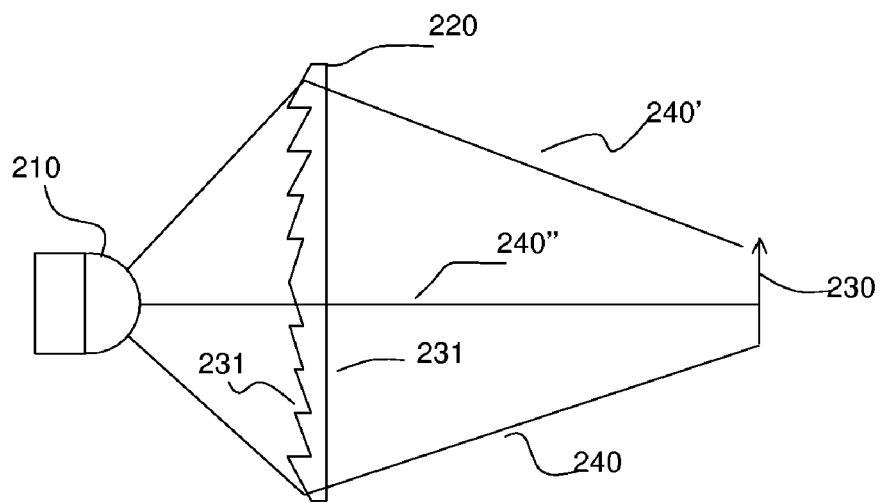
FIG. 2 shows an embodiment of the optical device using current invention.

FIG. 2 illustrates an embodiment of the present invention for LED curing source comprising a single high power LED 210 and a Fresnel lens 220 that focuses the illuminating light from the LED to a diffraction limited spot 230. The high power LED 210 preferably has an optical output power approximately between 400-800 mW, such as that Luxeon V produced by Lumiled at a wavelength in range of 400-500 nm. Higher powers are preferred since they provide faster and deeper curing time. The illumination rays 240, 240', and 240" illustrate the function of the lens in collecting radiation and focus to a curing spot.

The Fresnel lens consists of a groove side 231 and a flat side 230. The grooves are circular cylindrical portions intersected by conical portions manufactured by standard machine processes such as diamond turning, injection and compression molding. They maintain the contour of the refracting surface of a conventional lens while removing the bulk of material between the refracting surfaces. The groove side of the Fresnel lens is preferably in the receiving direction of the optical illumination and the flat side in the outward direction to avoid surface damage in an assembly. Constant groove spacing or constant groove heights can be used in the design of the Frensnel lens. Compared to aspheric lens, Fresnel lens can be 10 times thinner which is critical to the application for close distance focus. Depending on the shapes of the grooves, a circular, square or narrow line focused spot can be realized at the focus spot 230 using circular or cylindrical lens.

Figure 3:
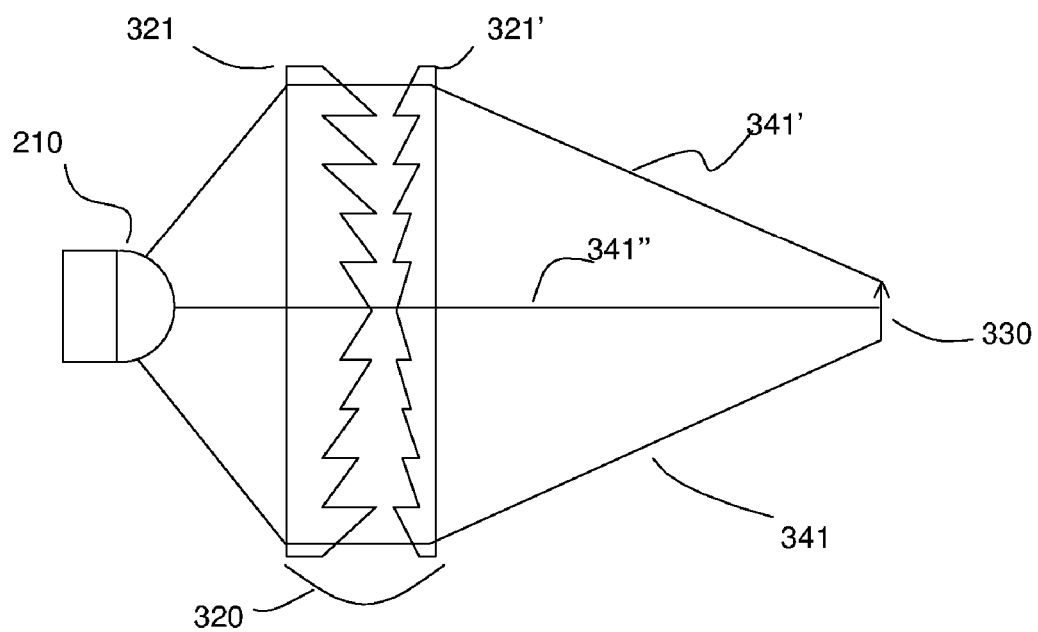
FIG. 3 shows another embodiment of the optical device using current invention.

FIG. 3 illustrates another preferred embodiment of the present invention for LED curing source consisting of a single high power LED 210 and a Fresnel lens pair 320 that focuses the illuminating light 341, 341' and 341" to a spot 330. Compared with a single Frensnel lens in FIG. 2, the Fresnel lens pair 320 is more efficient in which it acts as a condenser lens consisting of a collimating lens 321 and a focusing lens 321'. The collimating lens 321 is placed at a focal distance from the LED source 210 between 2 to 10 millimeters or preferably between 2 to 5 millimeters to collimate the source light to diffraction limited collimation beam. While closer distance from the lens to the LED source chip reduces the size of the lens required, typical LED chips are packaged with glass dome lens with a size in the range of 1 to 3 millimeters limiting the proximity of the lens to the source. Additionally, avoidance of heat dissipated directly from the chip will limit the proximity of the lens to the LED as well.

The Fresnel lens 321 should maximize collection efficiency while balancing the size limitation of the instrument. A good parameter of the lens performance is described by optical F numbers as defined in:

$$F\text{ number}=f/D$$

where the F number is the ratio of the focal length of the lens divided by the beam diameter of the lens. Smaller F number provides higher collection efficiency in angular distributed radiations. The use of Fresnel lens enables a much faster lens with F number of approximately between 0.1 and 2 or below 0.3 that can collect the Lambertian illumination from the LED up to 120 to 160 degrees as compared with typical aspheric lens with F number above 0.5 which collects radiation below 70 degrees. This minimizes loss during coupling as is often encountered in the fiber waveguide coupling and aspheric lens coupling.

The focus lens 321' is placed in close proximity parallel to the collimating lens 321 with a focal length determined by working distance of a particular application. For dental curing applications, the focal length of the focusing lens 321' is preferably between 2 to 20 millimeters optimizing the efficiency at a working distance of 2 to 20 millimeters. The Fresnel lens pair also effectively works as a single lens with very short focal length of below 2 millimeters and very thin thickness as small as 0.5 millimeters, which are critical to both minimizing diffraction loss and making compact devices.

The Fresnel lens pair 320 is preferably formed by a groove out Fresnel lens 321 and a groove in Fresnel lens 321' bonded together to form a thin sheet lens 320 with flat outside surfaces. Such arrangement eases mounting of the Fresnel lens pair 320 into a lens cell that attaches to the LED mount in addition to improve scratch resistance to the active Fresnel groove surface.

Figure 4:
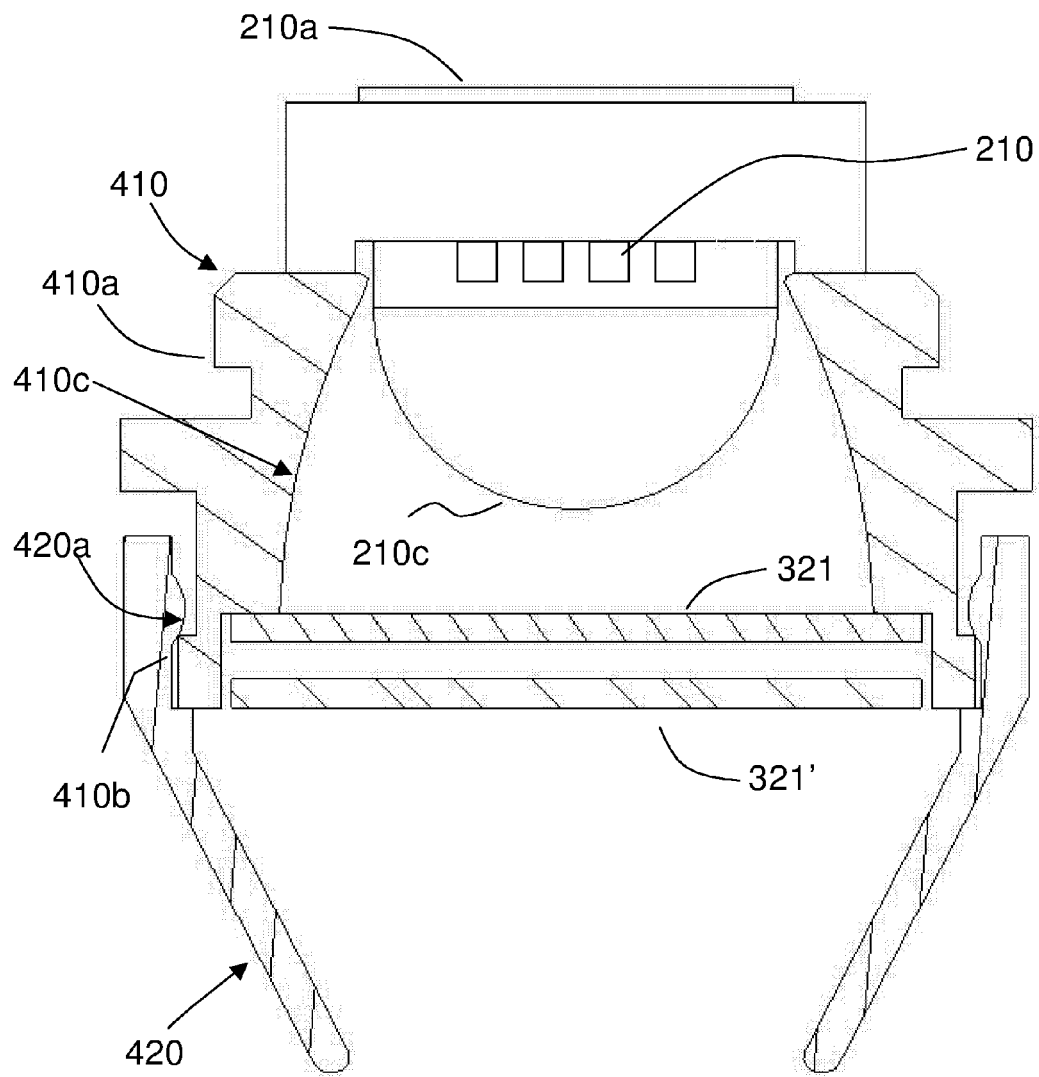
FIG. 4 shows an embodiment in implementing the optical device using current invention.

FIG. 4 illustrates a proposed implementation of the present invention for LED curing source consisting of a high power LED 210 with multiple diode chips packaged in a single diode, directional collimating hyper-spherical lens 210c, diode heat sink 210a, a Fresnel lens pair 321 and 321', a mounting parabolic reflector 410, and a disposable curing cap 420. The light emitted from LED 210 typically has a divergence angle of over 80 degrees after lens co-packaged lens 210c.

The parabolic reflector 410 redirects the high divergence angle beam to a near collimated beam. The reflector 410 is consisted of a mounting thread 410a, a high reflectance inner surface 410c, and a cap stopper 410b. The mounting threads 410a mounts the LED illumination optic module to a handpiece head as will be discussed in detail in FIG. 7. The high reflectance surface 410c provides reflectivity of over 95, for example 98%, at the LED emitted wavelength range. Example materials for 410 are copper, aluminum and plastics. Electroplating of copper with chromium, zinc, aluminum, and silver offers the best reflectivity. Alternatively, high reflective thin films such as multiplayer metal oxide or polymer films can be evaporated or coated and post mounted at the inner surface 410c to achieve the desired results.

The proposed lens 321 and 321' are thin disks of Fresnel lenses. The embodiment of the current invention enables collimation of LED illumination with minimum coupling loss, focus of the beam to a desired spot size limited by diffraction from source chip size and a minimum thickness in the lens assembly. The Fresnel lens consists of circular grooves that refract light with different angle at different radial position to form the function of a lens. They can be formed by either constant grooves spacing or constant groove height. Constant groove height is preferred for the Fresnel lens in curing applications to allow bonding of the two lenses forming the condenser lens into a single lens sheet with grooves facing each other as shown in FIG. 3 and flat surface on their outside.

The Fresnel lens can be made of transparent materials such as polycarbonate, acrylic, silicone, rigid vinyl and others that are low cost through compression or injection molding of large piece of materials enabling wafer level productions that make them low cost. The lens pair can be assembled together through standard packaging procedures such as bonding at individual on wafer level. Single lens can be also used in the case of highly collimating beam from the hyper-spherical lens 210c and parabolic reflector 410c.

The disposable and sterilizable curing cap 420 provides isolation of curing tip from patients or objects under treatment. It is conveniently snapped on the surface of the mounting reflector 410 and stopped by a mechanical edge stopper 410b. The length of the lens cap 420 is shorter than the focal length of the second Fresnel lens 321'. The lens cap 420 provides stray light shield with proper doping of the cap materials to absorb the wavelength of the illuminated light from the LED. It can also be attached with a third Fresnel lens at the exit window to further improve the working distance of the curing light. The lens cap is preferably made of materials that are disposable such as acrylic, polycarbonate and other plastics through standard manufacturing processes such as injection molding. It further provides a means to sterilize or dispose the cap at a minimum cost.

Figure 5:
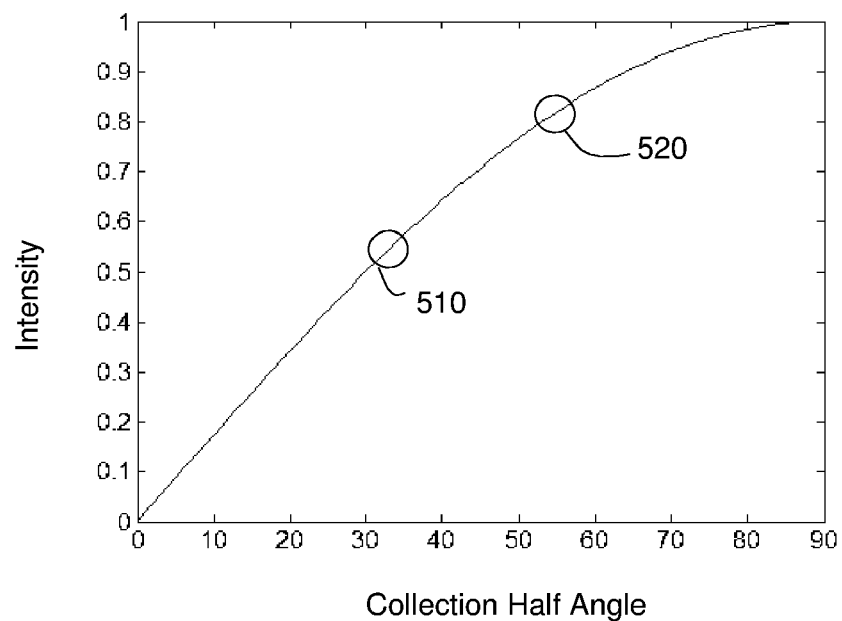
FIG. 5 shows the differences in collection angle using the current invention compared to prior art.

FIG. 5 compares theoretical performance of the current invention with the prior art dental curing device using a single aspheric lens. The calculation shows the radiation intensity as a function of radiation angle relative to the axis normal to the LED mounting surface. The prior art aspheric lens typically limit collection angle below +/−35 degrees at collection efficiency of 50% indicated by 510 while the current invention can increase the collection angle of the radiation above +/−60 degrees indicated by 520 with collection efficiency up to 90%.

Figure 6:
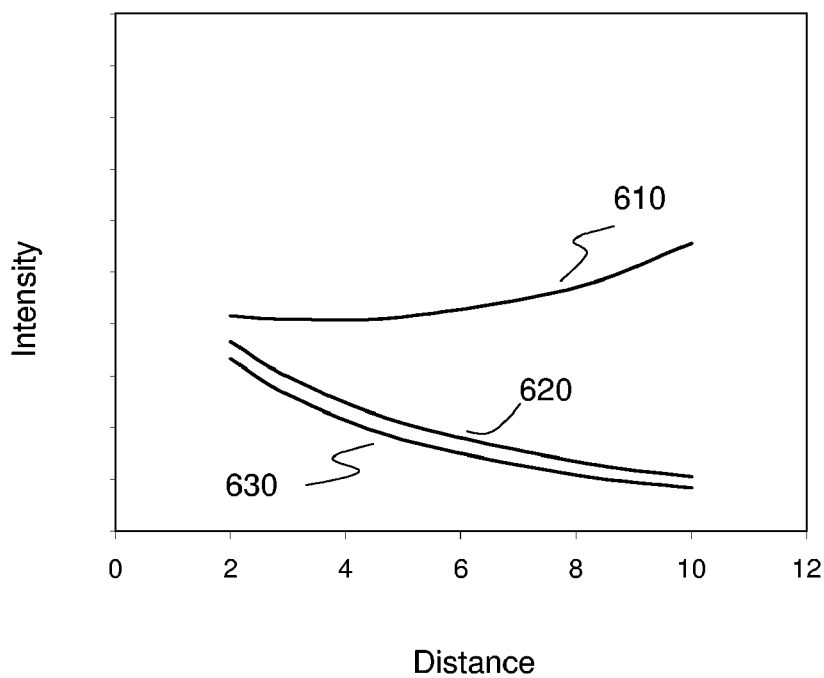
FIG. 6 illustrates curing light intensity as a function of the distance from the curing apparatus to the curing object using current invention compared to prior art.

FIG. 6 shows the curing light intensity (power density) as a function of the distance from the output window of the curing units to the object. Compared with conventional curing units using fiber optic guide 630 and bulk aspheric lens 620, the current invention 610 maintains and optimizes curing intensity between 2 to 10 mm through minimized diffraction and optimized beam focusing. The light intensity at 10 mm of the current invention is more than five times that of the prior art approaches ensuring maximum curing at desired locations.

Figure 7:
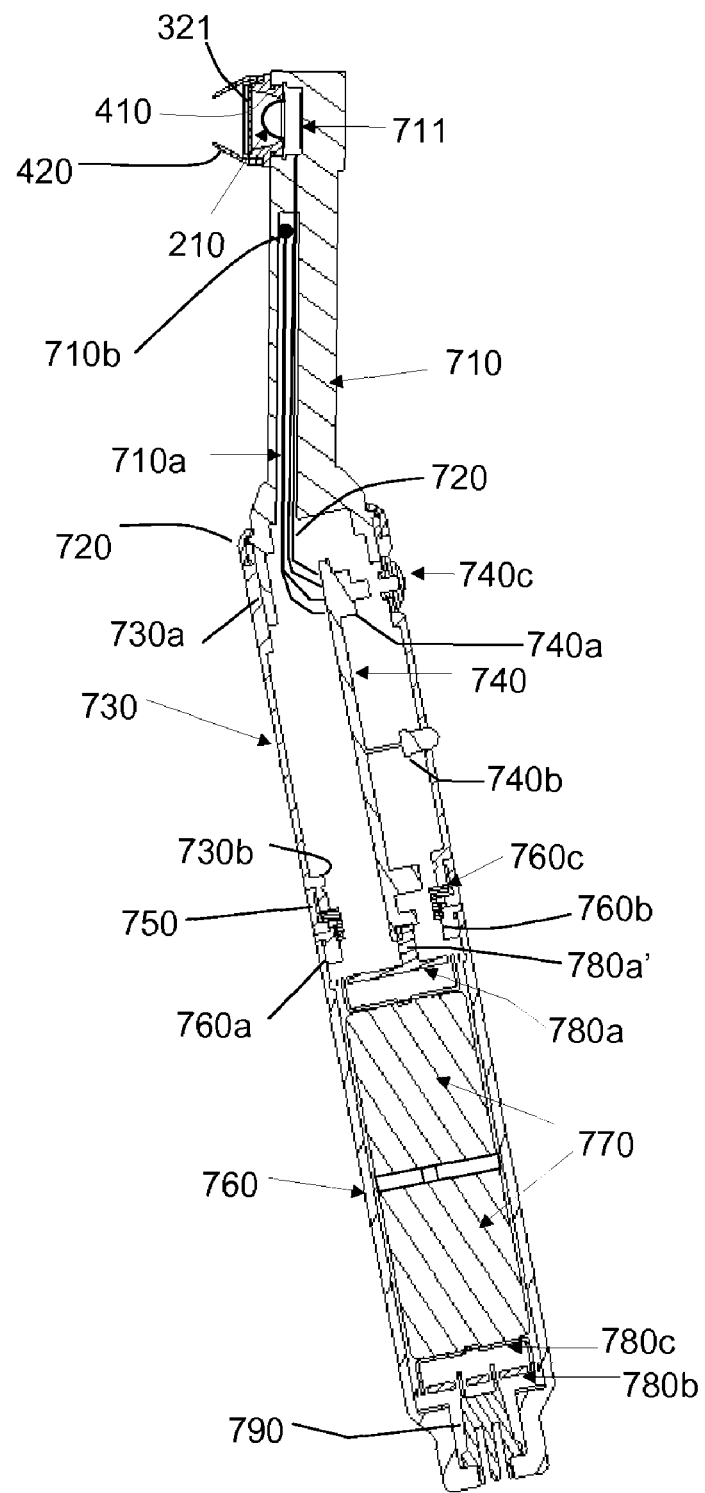
FIG. 7 shows an embodiment of a cordless dental LED curing device using the current invention.

FIG. 7 illustrates an embodiment of the current invention in a high efficiency dental LED curing light consisting of an LED mounting head 710, a high power LED 210, a lens mounting reflector 410, Fresnel lens 321, a curing cap 420, a handpiece housing consisting of a control board housing 730, a rechargeable battery housing 760 and a thread link ring 750 via a thread 730b. The mounting head 710 and the handpiece portion are preferably made of highly heat conductive materials such as aluminum and copper to enhance heat dissipation speed.

The LED head mount 710 provides heat dissipation to the LED generated powers through thermal interface 711 bonded by thermal epoxy between the back side of the LED 210 and the surface 711. The head mount 710 is attached to the handpiece body through threaded retainer 720 that clamps the two together at the interface 730a. The head mount 710 preferably has an angle from the handpiece to allow an angle of illumination, approximately between 5 to 45 degrees, for ease of access to mouth.

The LED 210 is powered by a control circuit board 740 by two lead wires 720 fed through a hole inside the head mount 710. The circuit board 740 resides in the main control housing 730. Circuit board 740 is activated by an on-off switch button 740a through a touch button 740c and is powered by a plurality of rechargeable batteries 770. Circuit board 740 performs DC-DC conversion to provide the desired current for the LED 210 in addition to controlling a preset exposure timing sequence, controlling thermal protection of LED 210 against high temperatures using signals received from a thermal sensor 710b placed in close proximity to the LED 210 and connected by two lead wires 710a, controlling low battery indicator LED 740b and controlling automatic shut off.

A plurality of rechargeable batteries 770 is housed in the battery compartment 760. The batteries interface with two circular board 780a and 780b via a pair of contact pins 780c and are held tight into the compartment 760 by a ring 760b via thread 760a. A clamp ring pushes the connect ring 750 tight against the ring 760b via a connecting ring 760c. The circuit board 780a interfaces with the main control board 740 via a plug-in pin connector 780a'. The circuit board 780b interfaces an external power adapter through a small pin connector 790. The combined circuit boards 740, 780a, and 780b also provide a smart charging circuit to safely charge the rechargeable batteries 770.

The rechargeable battery is preferably lithium ion battery that has 3.7V per battery. A single battery with sufficient energy capacity is typically sufficient for dental curing light operation although multiple batteries can extend the standalone operation time.

The proposed high efficiency LED curing device enables low cost and efficient curing of photosensitive materials. The device is particularly useful for portable handheld dental curing light. It will be apparent to those skilled in the art that various modifications and variations can be made to the present invention without departing from the spirit and scope of the invention. Thus it is intended that the present invention covers the modifications and variations of this invention provided they come within the scope of the appended claims and their equivalents.

What is claimed is:

1. A curing light apparatus for curing a light activated composite, comprising:
    a plurality of LED sources configured to collectively emit a divergent curing light adapted to cure the light activated composite;
    a lens mounting reflector having a high reflectance inner surface and configured adjacent to the plurality of LED sources to reflect a portion of the divergent curing light;
    a Fresnel lens pair including a first Fresnel lens and a second Fresnel lens, adjacent to each other in cascaded series and configured to focus the divergent curing light, the Fresnel lens pair directly secured with respect to the lens mounting reflector and configured to direct the focused curing light directly to the composite;
    the first Fresnel lens has a focal length of approximately between about 2 to about 10 millimeters and is configured to collect and collimate the divergent curing light from each of the plurality of LED sources; and
    the second Fresnel lens has a focal length of approximately between about 2 to about 20 millimeters and is configured to focus the collimated curing light to the composite with increasing intensity as a function of distance.

2. The apparatus of claim 1 further comprising:
    a LED mounting head wherein the plurality of LED sources are mounted thereto; and
    a body secured to the LED mounting head.

3. The optical apparatus of claim 2, wherein the lens mounting reflector comprises:
    a mounting thread configured to secure the lens mounting reflector to the LED mounting head; and
    a parabolic cylindrical inner reflecting surface providing reflectivity of approximately over 95% across emitted wavelengths of the plurality of LED sources;
    wherein the parabolic cylindrical inner reflecting surface is comprised of high reflectance materials selected from the group of: plated, coated and bonded aluminum, chromium, zinc, silver, multilayer metal oxide thin films, and polymer films.

4. The apparatus of claim 2, wherein the body comprises;
    a rechargeable battery;
    a plurality of circuit boards; and
    means for activating the circuit boards.

5. The apparatus of claim 1, wherein the plurality of LED sources are configured to emit the divergent curing light with an optical power of approximately between 100 mW to 800 mW at a wavelength of approximately between 300 to 500 nm.

6. The apparatus of claim 1 further comprising a lens cap configured to be selectively disposed about the Fresnel lens pair and the focused curing light, the lens cap having a length shorter than a focal length of the second Fresnel lens.

7. The optical apparatus of claim 1, wherein the first Fresnel lens and the second Fresnel lens each comprise a circular cylindrical disk including circular grooves, wherein the first Fresnel lens has a first flat side facing the plurality of LED sources and a second opposing grooved side, and the second Fresnel lens has a first grooved side facing the first Fresnel lens and a second opposing flat side.

8. The optical apparatus of claim 1, wherein the first Fresnel lens and the second Fresnel lens each have a thickness of approximately between 0.1 to 5 millimeters and each have an F number of approximately between 0.1 and 2.

9. The apparatus of claim 1, wherein the first Fresnel lens and the second Fresnel lens are each comprised from one of a material selected from the group consisting of: polycarbonate, acrylic, rigid vinyl, and polyacrylic.

10. A method of making a dental LED curing light apparatus comprising the step of:
    supplying a plurality of LED sources to emit divergent curing light;
    supplying a lens mounting reflector and a high reflectance inner surface and configured adjacent to said plurality of LED sources;
    supplying a Fresnel lens pair including a first Fresnel lens to collimate and a second Fresnel lens to focus the divergent curing light, the Fresnel lenses adjacent and parallel to each other in cascaded series and mounted on said lens mounting reflector to direct the curing light directly to a composite;
    said first Fresnel lens has a focal length approximately between 2 to 10 millimeters to collect and collimate said divergent curing light from said plurality of LED sources simultaneously;
    said second Fresnel lens has a focal length approximately between about 2 to about 20 millimeters to focus said collimated curing light to said composite with increasing intensity as a function of distance; and
    said lens mounting reflector is made of one or more materials comprising copper, aluminum and plastics.

11. The method of claim 10, wherein said plurality of LED sources emit the divergent curing light with optical power approximately between 100 to 800 mW at a wavelength approximately between 300 to 500 nm.

12. The method of claim 10, wherein each Fresnel lens of said Fresnel lens pair are made from one or more materials selected from the group consisting of polycarbonate, acrylic, rigid vinyl, and polyacrylic.

13. The method of claim 10, wherein said lens mounting reflector comprises a parabolic cylindrical inner reflecting surface made from one or more high reflectance materials comprising plated, coated and bonded aluminum, chromium, zinc, silver and multiplayer metal oxide thin films and polymer films that provide reflectivity of approximately over 95% across emitted wavelengths of said plurality of LED sources.

14. A curing light apparatus for curing a light activated composite, comprising:
    a plurality of LED sources configured to collectively emit a divergent curing light adapted to cure the light activated composite;
    a lens mounting reflector having a high reflectance inner surface and configured adjacent to the plurality of LED sources to reflect a portion of the divergent curing light;
    a Fresnel lens pair including a first Fresnel lens and a second Fresnel lens, adjacent to each other in cascaded series and configured to focus the divergent curing light, the Fresnel lens pair directly secured with respect to the lens mounting reflector and configured to direct the focused curing light directly to the composite;

the first Fresnel lens has a focal length of approximately between about 2 to about 10 millimeters and is configured to collect and collimate the divergent curing light from each of the plurality of LED sources;

the second Fresnel lens has a focal length of approximately between about 2 to about 20 millimeters and is configured to focus the collimated curing light to the composite with increasing intensity as a function of distance;

a LED mounting head wherein the plurality of LED sources are mounted thereto;

a body secured to the LED mounting head; and wherein the plurality of LED sources are configured to emit the divergent curing light with an optical power of approximately between 100 mW to 800 mW at a wavelength of approximately between 300 to 500 nm.

15. The apparatus of claim 14 further comprising a lens cap configured to be selectively disposed about the Fresnel lens pair and the focused curing light, the lens cap having a length shorter than a focal length of the second Fresnel lens.

16. The apparatus of claim 14, wherein the first Fresnel lens and the second Fresnel lens each comprise a circular cylindrical disk including circular grooves, wherein the first Fresnel lens has a first flat side facing the plurality of LED sources and a second opposing grooved side, and the second Fresnel lens has a first grooved side facing the first Fresnel lens and a second opposing flat side.

17. The apparatus of claim 14, wherein the first Fresnel lens and the second Fresnel lens each have a thickness of approximately between 0.1 to 5 millimeters and each have an F number of approximately between 0.1 and 2.

18. The apparatus of claim 14, wherein the lens mounting reflector comprises:

a mounting thread configured to secure the lens mounting reflector to the LED mounting head; and a parabolic cylindrical inner reflecting surface providing reflectivity of approximately over 95% across emitted wavelengths of the plurality of LED sources;

wherein the parabolic cylindrical inner reflecting surface is comprised of high reflectance materials selected from the group of: plated, coated and bonded aluminum, chromium, zinc, silver, multilayer metal oxide thin films, and polymer films.

19. A method of making a dental LED curing light apparatus comprising the step of:

supplying a plurality of LED sources to emit divergent curing light;

supplying a lens mounting reflector and a high reflectance inner surface and configured adjacent to said plurality of LED sources;

supplying a Fresnel lens pair including a first Fresnel lens to collimate and a second Fresnel lens to focus the divergent curing light, the Fresnel lenses adjacent and parallel to each other in cascaded series and mounted on said lens mounting reflector to direct the curing light directly to a composite;

said first Fresnel lens has a focal length approximately between 2 to 10 millimeters to collect and collimate said divergent curing light from said plurality of LED sources simultaneously;

said second Fresnel lens has a focal length approximately between about 2 to about 20 millimeters to focus said collimated curing light to said composite with increasing intensity as a function of distance;

said lens mounting reflector is made of one or more materials comprising copper, aluminum and plastics;

wherein said plurality of LED sources emit the divergent curing light with optical power approximately between 100 to 800 mW at a wavelength approximately between 300 to 500 nm, and wherein each Fresnel lens of said Fresnel lens pair are made from one or more materials selected from the group consisting of polycarbonate, acrylic, rigid vinyl, and polyacrylic.

20. The method of claim 19, wherein said lens mounting reflector comprises a parabolic cylindrical inner reflecting surface made from one or more high reflectance materials comprising plated, coated and bonded aluminum, chromium, zinc, silver and multiplayer metal oxide thin films and polymer films that provide reflectivity of approximately over 95% across e mitted wavelengths of said plurality of LED sources.

* * * * *